United States Patent [19]
Lafferty et al.

[11] Patent Number: 5,188,093
[45] Date of Patent: Feb. 23, 1993

[54] PORTABLE ARTHROSCOPE WITH PERISCOPE OPTICS

[75] Inventors: Michael Lafferty, Leucadia; Daniel Kline, Carlsbad; Charles S. Slemon, Encinitas, all of Calif.

[73] Assignee: Citation Medical Corporation, Reno, Nev.

[21] Appl. No.: 650,066

[22] Filed: Feb. 4, 1991

[51] Int. Cl.⁵ .............................. A61B 1/06
[52] U.S. Cl. ................................ 128/6
[58] Field of Search ............... 128/4, 5, 6, 398; 385/117, 119

[56] References Cited

U.S. PATENT DOCUMENTS

| | | | |
|---|---|---|---|
| 4,253,448 | 3/1981 | Terada | 128/4 |
| 4,589,404 | 5/1986 | Barath et al. | 128/6 |
| 4,590,923 | 5/1986 | Watanabe | 128/6 |
| 4,607,622 | 8/1986 | Fritch et al. | 128/6 |
| 4,620,769 | 11/1986 | Tsuno | 350/96.26 |
| 4,736,733 | 4/1988 | Adair | 128/6 |
| 4,754,328 | 6/1988 | Barath et al. | 358/98 |
| 4,755,873 | 7/1988 | Kobayashi | 358/98 |
| 4,762,120 | 8/1988 | Hussein | 128/6 |
| 4,782,819 | 11/1988 | Adair | 128/6 |
| 4,844,071 | 7/1989 | Chen et al. | 128/6 |
| 4,867,138 | 9/1989 | Kubota et al. | 128/6 |
| 4,920,961 | 5/1990 | Grossi et al. | 606/14 |
| 4,947,245 | 8/1990 | Ogawa et al. | 358/98 |
| 5,005,943 | 4/1991 | Fort | 128/4 |

Primary Examiner—Cary E. O'Connor
Attorney, Agent, or Firm—Nydegger & Associates

[57] ABSTRACT

A hand-held portable arthroscope has a camera assembly and a disposable scope assembly rotatably attached to the distal end of the camera assembly. A probe which includes a fiber optic image guide and a plurality of optical illuminating fibers is rotatably mounted on the scope assembly, and is insertable into a body for imaging the internal structure of the body. The illuminating fibers extend through the scope assembly and are connected in light communication with a quartz halogen lamp for illuminating the internal body structure being imaged. To gather light from the illuminated internal structure of a body into which the probe has been inserted, a GRIN rod is attached to the distal end of the image guide. The image guide is bent near its distal end to offset the axis of the GRIN rod from the axis of the camera assembly, to enhance the field of view of the arthroscope when the scope assembly, which supports the image guide with GRIN rod, is rotated. Focussing optics are mounted in the camera assembly in light communication with the image guide. These focussing optics are axially movable within the camera assembly for focussing the image from the image guide. Light which passes through the focussing optics enters a camera head which is also mounted in the camera assembly. The camera head is in turn electrically connected to a video display device for producing an image of the internal structure of the body.

11 Claims, 3 Drawing Sheets

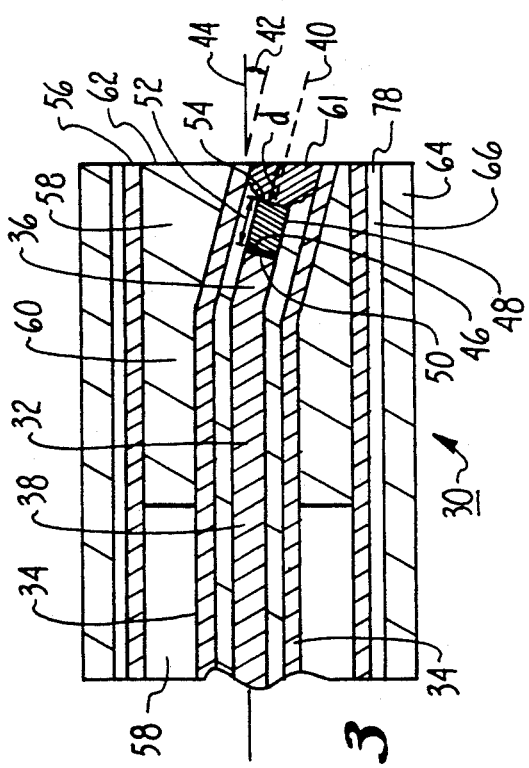
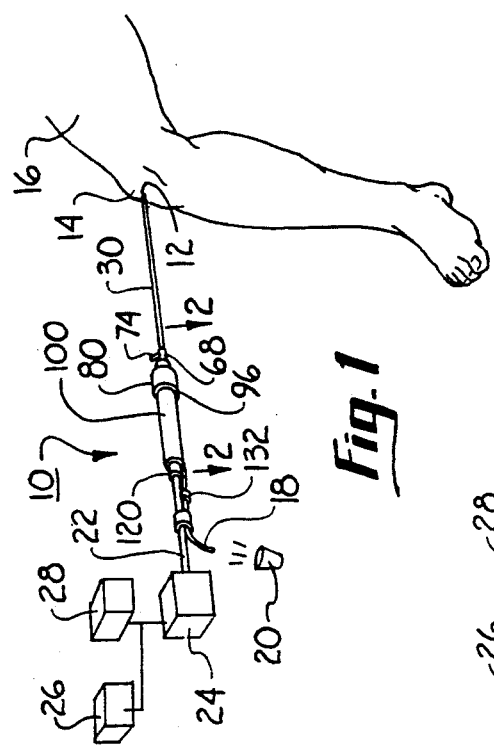
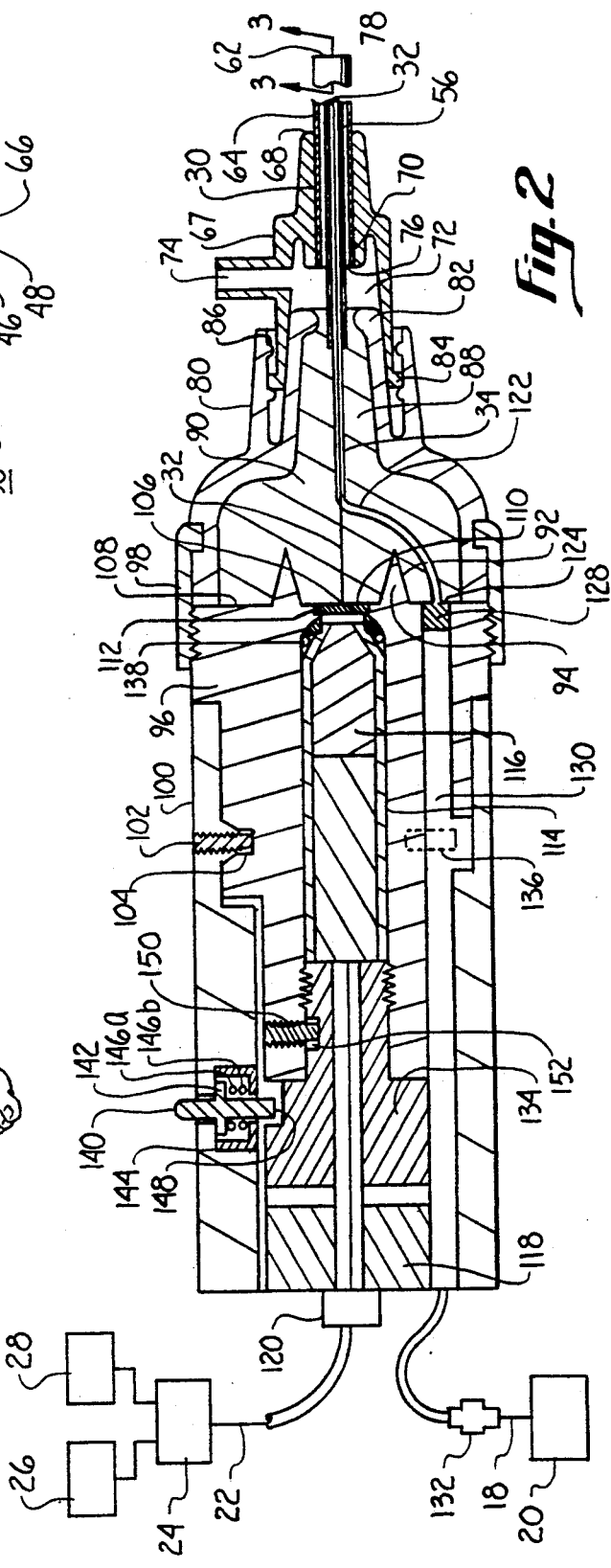

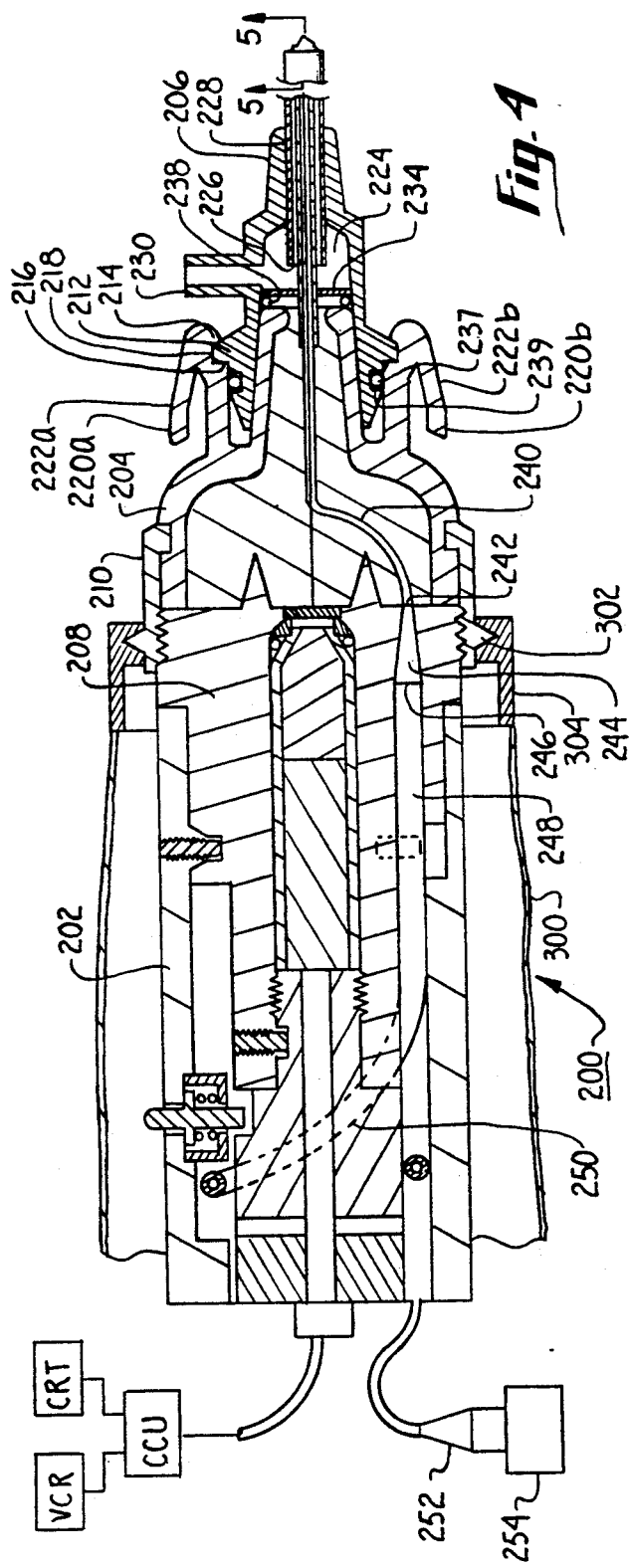

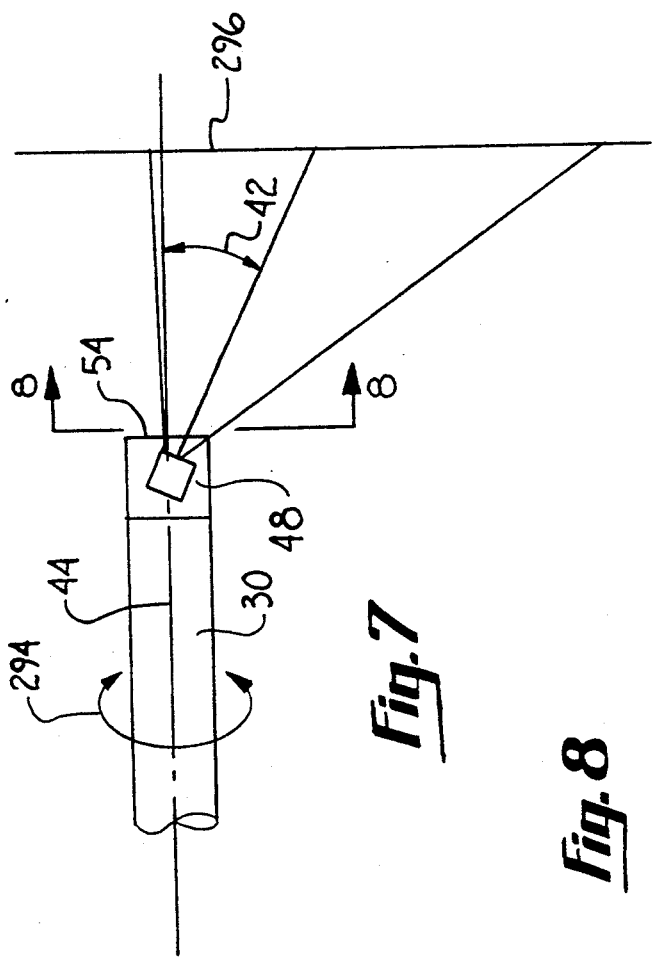
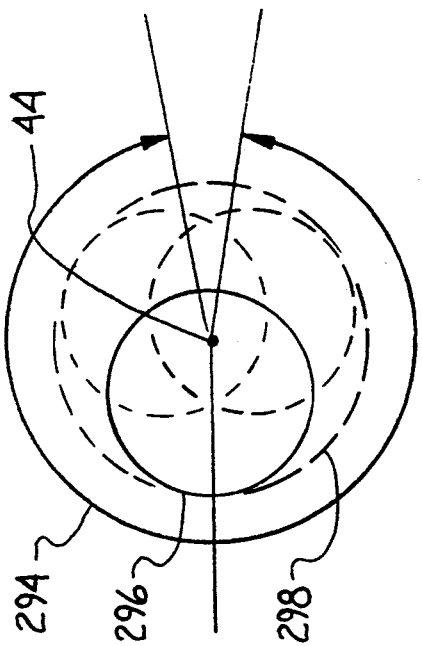

PORTABLE ARTHROSCOPE WITH PERISCOPE OPTICS

FIELD OF THE INVENTION

The present invention relates generally to medical diagnostic devices. More particularly, the present invention relates to arthroscopes. The present invention particularly, though not exclusively, relates to hand-held portable arthroscopes for viewing a relatively large area within a body joint.

BACKGROUND OF THE INVENTION

In the area of medicine, modern surgical techniques have been developed for diagnosing and correcting damage to the interior structure of body parts, e.g., bone joints. One of these modern surgical techniques is arthroscopy, which can be used for examining the interior structure of a body joint, for example, a knee, in order to determine the extent of any damage to the joint. In other words, arthroscopy permits viewing the internal structure of a body joint without requiring conventional surgery on the joint. If required, relatively non-invasive corrective surgery can be performed in conjunction with arthroscopic examination techniques to repair joint damage which is discovered during the examination.

Arthroscopic examination typically involves inserting a probe into the joint to be examined. The probe has an imaging device attached to it, and the imaging device is in turn connected through the probe to a video display for generating a picture of the interior structure of the joint. Consequently, the operator of the arthroscope is able to view, real-time, the interior structure of the joint as the probe is inserted into the joint. By viewing the internal structure of the joint, a diagnosis of any damage to the joint can be made and appropriate treatment prescribed.

It is the case that existing arthroscopes require support equipment which is relatively large and bulky and which is typically permanently installed for use in an operating room. Consequently, these arthroscopes cannot be easily moved from one location to another, as may occasionally be required in a medical establishment. Furthermore, arthroscopes which require sizable support equipment are ordinarily expensive devices, and their relatively high cost can make arthroscopic examination cost prohibitive for some patients. The present invention recognizes that an arthroscope need not require large and expensive support equipment and that there is a need to provide an arthroscope which can be used in a Doctor's office for diagnosis of a joint injury. Further, there is a recognized need to provide an arthroscope with a sufficiently small disposable probe so that only a local anesthetic is necessary.

Additionally, the probes of existing arthroscopes are typically reusable devices and must accordingly be sterilized before each use, in order to eliminate the possibility of infecting the arthroscopy patient with a contaminated probe. Unfortunately, the possibility remains that a reusable probe may not be effectively sterilized and can accordingly remain septic, or that a properly sterilized probe could become septic in the time period between sterilization and use of the probe. The present invention recognizes that an arthroscope can be provided which uses a non-reusable probe to substantially reduce the likelihood of transmitting infections.

In addition to the above considerations, it is also desirable for the arthroscope to have a relatively wide field of view when the probe of the arthroscope is positioned within the joint. This is in order to maximize the size of the internal body area which the arthroscope operator can examine. Providing a wide field of view simply by enlarging the lens of the arthroscope, however, would be counterproductive since the introduction of a larger lens would require a larger entry site into the knee. A larger entry site, however, is to be avoided. Accordingly, it is desirable that the arthroscope be capable of viewing a relatively large area within a joint, without requiring the use of a comparatively large arthroscope lens.

It is accordingly an object of the present invention to provide an arthroscope which is portable and hand-held. It is a further object of the present invention to provide an arthroscope which has a disposable probe that is insertable into a body joint for generating a real-time picture of the joint. It is also an object of the present invention to provide an arthroscope which can view a relatively large portion of the internal structure of a joint. Finally, it is an object of the present invention to provide an arthroscope which is relatively inexpensive to manufacture and comparatively easy and cost-effective to use.

SUMMARY

A portable diagnostic arthroscope has a hand-held generally cylindrical hollow camera assembly and a disposable scope assembly removably attached to the distal end of the camera assembly. The disposable scope assembly can be rotated relative to the camera assembly. Further, an elongated probe is rotatably attached to the disposable scope assembly.

More specifically, the probe includes a hollow tubular steel cannula which is mounted on a base assembly. The cannula extends beyond the distal end of the base assembly, and the base assembly is rotatably engaged with the scope assembly, so that the base assembly, with its cannula, can be rotated relative to the scope assembly. The cannula itself has an open distal end and an open proximal end, so fluid can be introduced into the base assembly and directed through the cannula to bathe the internal joint structure.

In accordance with the present invention, a cylindrically-shaped GRIN rod is attached to the end of a scope needle which is slidably introduced through the cannula to position the GRIN rod inside the cannula near the cannula's open distal end. Light which is reflected by the interior structure of the joint enters the distal base of the cylindrically-shaped GRIN rod and is focussed by the GRIN rod onto the GRIN rod's proximal base.

To transfer the light back through the scope needle, the proximal base of the GRIN rod is attached to the distal end of a fiber optic image guide. This image guide extends through the scope needle which is part of the scope assembly. Light which enters the distal base of the GRIN rod is focussed by the GRIN rod onto the image guide. Importantly, the image guide is bent near its distal portion to form an angle of about twenty-five (25) degrees between the distal portion of the image guide and the axis of the probe. Consequently, the axis of the GRIN rod, which is attached to the distal end of the image guide, is not parallel to the axis of the probe. Accordingly, when the scope assembly is turned to rotate the image guide about its axis, the distal base of the GRIN rod is moved through a donut-shaped swath which enables the GRIN rod to scan a relatively large area of the internal structure of the joint.

The image guide is optically joined to focussing optics which are mounted in the camera assembly. These focussing optics are axially movable within the housing for focussing the image from the image guide onto the camera head in the camera assembly. Thus, the focussing optics are optically joined with a camera head which is mounted in the camera assembly and which is electrically connected to a camera control unit external to the arthroscope. As envisioned by the present invention, the camera control unit can control a CRT or other visual display device to display the image of the internal structure of the joint.

Also, to illuminate the interior structure of the joint, a plurality of optical illumination fibers are mounted within the scope needle next to the image guide. These illumination fibers extend through the scope assembly and are joined with a first end of an optical cable that is mounted inside the camera assembly. In accordance with the present invention, the second end of the optical cable can be irradiated with light from a quartz halogen lamp or other suitable light source which can be located either in the scope assembly or the camera assembly, or located externally to the camera assembly. Thus, light from the lamp can be transmitted through the optical cable and illumination fibers to illuminate the internal structure of the joint.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 1 is a perspective view of the novel portable arthroscope of the present invention, seen in its intended environment;

FIG. 2 is a partial cross-sectional view of the novel portable arthroscope of the present invention, as seen along the line 2—2 in FIG. 1;

FIG. 3 is an enlarged cross-sectional view of the distal end of the probe of the novel portable arthroscope of the present invention shown in FIG. 2; as seen along the line 3—3 in FIG. 2;

FIG. 4 is a partial cross-sectional view of an alternate embodiment of the present arthroscope, as would be seen along the line 2—2 in FIG. 1;

FIG. 5 is an enlarged cross-sectional view of the distal end of the probe of the arthroscope shown in FIG. 4, as seen along the line 5—5 in FIG. 4;

FIG. 6 is an end view of the probe of the present invention;

FIG. 7 is a schematic view of the viewing area of the GRIN rod of the present invention; and FIG. 8 is a schematic view of the viewing area of the GRIN rod of the present invention, as seen in the direction of arrow 8 in FIG. 7.

DESCRIPTION OF THE PREFERRED EMBODIMENT

Referring initially to FIG. 1, a portable hand-held arthroscope is shown, generally designated 10. As shown, a portion of arthroscope 10 is inserted at an entry site 12 into a knee 14 of patient 16 to examine the internal structure of the knee 14. Arthroscope 10 is in light communication via optical line 18 to a quartz halogen lamp 20. While the present invention envisions use of a lamp 20 which is a quartz halogen lamp for economy, it is to be understood that lamp 20 may alternatively be any other suitable type of light source well known in the art, e.g., a xenon gas bulb.

FIG. 1 also shows that arthroscope 10 is electrically connected via line 22 to a camera control unit 24. Camera control unit 24 can in turn be electrically connected to a cathode ray tube (CRT) 26 and a video camera recorder (VCR) 28, as shown in FIG. 1, for respectively displaying and recording a video image of the internal structure of knee 14.

Now referring to FIGS. 2 and 3, the details of arthroscope 10 can be seen. As shown in FIG. 2, arthroscope 10 includes a probe 30 which is insertable into knee 14 (shown in FIG. 1). FIG. 3 shows that probe 30 includes a scope needle 56 which has an optical fiber image guide 32 which is coaxial with the scope needle 56 for most of its length. FIG. 3 further shows that probe 30 includes a plurality of optical illuminating fibers 34 which are positioned in the scope needle 56 around image guide 32. Preferably, both image guide 32 and illuminating fibers 34 are optical fibers which have relatively large numerical apertures (NA). Additionally, image guide 32 is preferably short, i.e., the length of image guide 32 is preferably less than about eight (8) inches.

As shown in FIG. 3, the distal segment 36 of image guide 32 is not collinear with the proximal segment 38 of image guide 32. More particularly, image guide 32 is bent so that the axis 40 of distal segment 36 forms an angle 42 of about twenty five (25) degrees relative to the axis 44 of proximal segment 38 and probe 30. Image guide 32 can be bent by heating a straight image guide (not shown) during the manufacturing process and then bending the image guide to the shape substantially as shown in FIG. 3.

Still referring to FIG. 3, the proximal end 46 of a cylindrical gradient refractive index (GRIN) rod 48 is bonded to the distal end 50 of image guide 32. Preferably, GRIN rod 48 is the type of internally-refractive lens made of thallium-doped glass manufactured by Nippon Sheet Glass. In accordance with the present invention, the length 52 of GRIN rod 48 establishes the focussing characteristics of GRIN rod 48 as appropriate for the particular application of arthroscope 10.

Importantly, as shown in FIG. 3, the distal end 54 of GRIN rod 48 defines a viewing window which is offset, i.e., not perpendicular to, axis 44 of probe 30 as a consequence of the bend formed in image guide 32. Stated differently, the axis 40 of distal segment 36 (and, hence, the axis of GRIN rod 48) is not parallel to the axis 44 of proximal segment 38 of image guide 32. Accordingly, when probe 30 (and, hence, image guide 32) is rotated in a manner to be subsequently disclosed, distal end 54 of GRIN rod 48 rotates through (and collects light from) a relatively large area. Consequently, it may be appreciated that by rotating probe 30, arthroscope 10 can examine a relatively large area of the internal structure of knee 14 (shown in FIG. 1).

Continuing with the description of structure shown in FIG. 3, probe 30 is shown to include a hollow scope needle 56 which has a lumen 58. As shown, needle 56 is positioned in a surrounding relationship with image guide 32 and illuminating fibers 34. Needle 56 is preferably a hollow 16-gauge stainless steel tube, and image guide 32 and illuminating fibers 34 are positioned in the lumen 58 of needle 56. The portion of lumen 58 which surrounds image guide 32 and illuminating fibers 34 is filled with an opaque epoxy material 60, to cushion and support image guide 32 and illuminating fibers 34 and to shield unwanted light from entering the image guide 32. Additionally, a clear epoxy 61 is placed in front distally from the GRIN rod 48 to permit light to enter the GRIN rod 48. It is to be appreciated in reference to FIG. 3 that end 62 of epoxy material 60 is preferably polished. As shown, distal end 54 of GRIN rod 48 is recessed a distance d from end 62. In the preferred embodiment, distance d is approximately five thousandths of an inch. Additionally, FIG. 3 shows that the portions of lumen 58 which is proximal to GRIN rod 48 is left open and is not filled with epoxy 60 in order to contain damage in the event probe 30 became inadvertently bent.

FIG. 3 further shows that probe 30 includes a 14-gauge hollow stainless steel cannula 64 which is positioned in a surrounding relationship to needle 56 with a passageway 66 between cannula 64 and needle 56 through which fluid can be infused.

Referring back to FIG. 2, cannula 64 of probe 30 is shown attached to a disposable injection-molded hub 67 near proximal end 70 of probe 30 to establish cannula assembly 68. Cannula assembly 68 is formed with a chamber 72, and fluid can be pumped into chamber 72 through fluid port 74 from a fluid source (not shown). Fluid in chamber 72 can enter open end 76 of cannula 64 and pass through passageway 66. This fluid can subsequently be flushed out of open end 78 (shown in FIG. 3) of cannula 64 to bathe the internal structure of knee 14 to provide a clear viewing field when probe 30 is inserted into knee 14.

Cannula assembly 68 is rotationally engageable with a disposable hollow injection-molded scope assembly 80, as shown in FIG. 2. More specifically, bulb portion 82 of scope assembly 80 extends into cannula assembly 68, and luer ears 84 of cannula assembly 66 can be threadably engaged with luer fitting 86 of scope assembly 80. As shown in FIG. 2, scope assembly 80 has a chamber 88 which is filled with a resilient epoxy material 90. Epoxy material 90 is in turn formed with key guides 92. Key guides 92 are configured for engaging the keys 94 which protrude from a front tube 96. More specifically, keys 94 of front tube 96 engage key guides 92 of epoxy material 90 to establish a predetermined orientation of front tube 96 relative to epoxy material 90. This predetermined orientation ensures that the optical components in scope assembly 80 are properly aligned with associated optical components in front tube 96 when scope assembly 80 is joined to front tube 96.

To hold scope assembly 80 against front tube 96, arthroscope 10 includes a retainer ring 98 which is slidably engaged with scope assembly 80 and threadably engageable with front tube 96 to removably connect scope assembly 80 to front tube 96. Furthermore, as shown in FIG. 2, front tube 96 is rotatably positioned in a camera assembly 100 and is held axially stationary with camera assembly 100 by retaining screw 102. More particularly, retaining screw 102 is threadably engaged with camera assembly 100 and extends into a groove 104 which circumscribes front tube 96. Consequently, front tube 96 can be rotated relative to housing 100.

In describing the optical path through arthroscope 10, reference is made to FIG. 2, which shows that image guide 32 extends through epoxy material 90 of scope assembly 80. As shown, end 106 of image guide 32 is substantially coplanar with surface 108 of epoxy material 90. In accordance with the present invention, surface 108 is polished to a smooth finish to establish an image plane 110.

Light from image guide 32 which passes through image plane 110 impinges upon a transparent sapphire window 112. It is to be appreciated in reference to FIG. 2, that window 112 is fixedly mounted on front tube 96. It is to be further appreciated that window 112 is made of a material, i.e., sapphire, that is easy to clean yet hard to scratch. Additionally, an optics base 114 is slidingly positioned in front tube 96. Optics base 114 holds a focussing optic 116 which is in light communication with sapphire window 112. Thus, light which has passed through sapphire window 112 can enter focussing optic 116. Preferably, focussing optic 116 magnifies light from sapphire window 112 approximately seven times (7×) and focuses the light onto a camera head 118 which is also mounted in optics base 114. In the preferred embodiment, camera head 118 is a charged coupled device (CCD).

In accordance with the present invention, camera head 118 converts the light image from focussing optics 116 to an electrical signal representative of the internal structure of knee 14. This electrical signal is coupled into an appropriate electrical connector 120. As disclosed above, the electrical signal is conducted via line 22 to CCU 24 for further processing.

In describing the structure of arthroscope 10 which is used for illuminating the interior of knee 14, reference is made to FIG. 2, which shows that illuminating fibers 34 extend through epoxy material 90 in a fiber bundle 122 to end 108 of epoxy material 90. As shown, when the cap 80 is engaged with front tube 96, end 124 of fiber bundle 122 is juxtaposed with an illumination GRIN rod 128 which is, in turn, connected to optical continuation fiber 130. Continuation fiber 130 is in turn coupled to an optical connector 132, and optical connector 132 is in light communication with lamp 20 through optical line 18.

As disclosed above, arthroscope 10 incorporates a periscope feature wherein scope assembly 80 can be rotated relative to camera assembly 100 to rotate probe 30, and to selectively focus the image present on image plane 110. More specifically, by rotating probe 30, distal base 54 of GRIN rod 48 rotates through a donut-shaped swath for viewing a comparatively large area within knee 14. Also, the present invention provides a capability for focussing the image present on image plane 110 when scope assembly 80 is rotated relative to camera assembly 100.

In describing the details of the structure of arthroscope 10 for rotating probe 30 and for focussing the light image which is present on image plane 110, reference is made to FIG. 2. Recall that retainer ring 98 holds scope assembly 80 onto front tube 96, and that front tube 96 can be rotated within camera assembly 100. If desired, to limit the rotational motion of front tube 96 relative to camera assembly 100° to 170° in both the clockwise and counter-clockwise directions, stop screws (only stop screw 136 shown in phantom in FIG. 2), can be threadably engaged with front tube 96 to contact retaining screw 102.

In accordance with the present invention, a focussing ring 134 is threadably engaged with front tube 96 and abuts optics base 114, and a resilient annular O-ring 138 is positioned between front tube 96 and optics base 114 to urge optics base 114 against focussing ring 134. Focussing ring 134 can be operated to urge against optics base 114 to move optics base 114 as appropriate for focussing the image from image plane 110 onto the camera head CCD 118.

More particularly, as shown in FIG. 2, a button 140 is reciprocally mounted in camera assembly 100. As shown, button 140 has a collar 142 which can abut camera assembly 100 to retain button 140 in camera assembly 100. Furthermore, a flange 144 is fixedly attached to camera assembly 100, and two biasing O-rings 146 a,b are positioned between flange 144 and collar 142 of button 140 to bias collar 142 of button 140 against camera assembly 100 and provide a water seal. When button 140 is depressed, end 148 of button 140 contacts focussing ring 134 to hold ring 134 stationary relative to camera assembly 100. Thus, with button 140 depressed, when scope assembly 80 (and, hence, front tube 96) is rotated relative to camera assembly 100 scope assembly 80 is also rotated relative to focussing ring 134, which is being held stationary relative to camera assembly 100 by button 140. Consequently, stationary focussing ring 134, which is threadably engaged with rotating front tube 96, urges against optics base 114 to cause optics base 114 to move axially relative to front tube 96, scope assembly 80, and hence, image plane 110. When optics base 114 (and, hence, optic 116) is appropriately moved relative to image plane 110, the optical image present on image plane 110 can be focused.

It will be appreciated in reference to the discussion above that when scope assembly 80 is rotated clockwise relative to camera assembly 100 and button 140 is depressed, ring 134 urges optics base 114 distally relative to image plane 110 (i.e., toward the right in FIG. 2). On the other hand, when scope assembly 80 is rotated counterclockwise relative to camera assembly 100 and button 140 is depressed, resilient O-ring 138 urges optics base 114 proximally relative to image plane 110 (i.e., toward the left in FIG. 2). Consequently, as optics base 114 is moved axially relative to scope assembly 80, the focussing optics 116 which are mounted in optics base 114 also move axially relative to scope assembly 80 (and, hence, image plane 110) to focus the image present on image plane 110.

On the other hand, when scope assembly 80 (and, hence, front tube 96) is rotated relative to camera assembly 100, and button 140 is not depressed, focussing ring 134 is not held stationary relative to optics base 114. Consequently, optics base 114 is not moved axially relative to image plane 110, and the focus of the image from image plane 110 does not change. Importantly, however, image guide 32 is rotated relative to camera assembly 100, so that the area "viewed" by GRIN rod 48 rotates within knee 14 through a relatively wide swath.

Finally, FIG. 2 shows that a screw 150 is threadably engaged with front tube 96. Furthermore, screw 150 extends into a slot 152 that is formed in focussing ring 134. It will be appreciated that the widths of screw 150 and slot 152 establish the range of axial travel of ring 134 relative to front tube 96. In the preferred embodiment ring 134 can travel axially relative to front tube 96 a distance of about twenty (20) thousandths of an inch.

Now referring to FIGS. 4 and 5, an alternate embodiment of the novel arthroscope of the present invention is shown and generally designated 200. It is to be understood that arthroscope 200 is in all essential respects identical with arthroscope 10, with the exceptions disclosed below. More particularly, arthroscope 200 includes a camera assembly 202, a scope assembly 204, and a cannula assembly 206. As shown, scope assembly 204 is removably attached to a front tube 208 by retainer ring 210, and front tube 208 is in turn rotatably mounted in camera assembly 202.

FIG. 4 shows that cannula assembly 206 is rotatably attached to scope assembly 204, and that cannula assembly 206 can be removed from scope assembly 204. More specifically, cannula assembly 206 includes an abutment 212 and scope assembly 204 includes a detent 214 and a stop 216 which together establish an annular space 218. As shown in reference to FIG. 4, cannula assembly 206 can be urged proximally toward scope assembly 204 to snappingly engage abutment 212 with space 218 between detent 214 and stop 216. In accordance with the present invention, when abutment 212 is engaged with space 218, cannula assembly 206 can be rotated relative to scope assembly 204. To disengage cannula assembly 206 and scope assembly 204, ends 220a, b of respective arms 222a, b of scope assembly 204 are urged radially inwardly, and cannula assembly 206 is pulled distally away from scope assembly 204.

As further shown in FIG. 4, cannula base assembly 206 includes a reservoir 224 which is in fluid communication with the open proximal end 226 of a cannula 228. As shown, a fluid line 230 can be attached to cannula assembly 206 in fluid communication with reservoir 224, for flushing fluid into proximal end 226 of cannula 228 and out of the distal end 232 of cannula 228 (shown in FIG. 5). To prevent fluid from cannula 228 from spraying the operator of arthroscope 200 when cannula assembly 206 is detached from scope assembly 204, a pierceable fluid seal 234 can be positioned in reservoir 224 substantially as shown. Scope needle 56, when inserted into cannula 228, will pierce through the fluid seal 234. Also, a retainer ring 238 is bonded to cannula assembly 206 to retain fluid seal 234 within reservoir 224. Furthermore, an annular o-ring 237 is positioned in groove 239 of cannula assembly 206 to provide an additional seal between reservoir 224 and the operator of arthroscope 10.

Still referring to FIG. 4, arthroscope 200 is shown to include a plurality of optical illumination fibers which are grouped in a fiber bundle 240. As shown, fiber bundle 240 extends through scope assembly 204 and is optically joined to the distal base 242 of a fiber optic taper 244. Taper 244 is shaped as a right circular conical frustum, and the distal base 242 of taper 244 has approximately half the area of the proximal base 246 of taper 244. Proximal base 246 of taper 244 is joined to an optical transmission fiber 248. It will be appreciated by the skilled artisan that taper 244 directs light from transmission fiber 248 into fiber bundle 240, to maximize the amount of light transmitted through fiber bundle 240 for illuminating the internal structure of the knee.

Preferably, optical transmission fiber bundle 240 has a higher numerical aperture than do the illumination fibers which constitute fiber bundle 248. In any case, the numerical apertures for both bundle 240 and 248 should be as high as possible. Additionally, as shown in FIG. 4, transmission fiber 248 includes a slack loop segment 250 to compensate for movement of transmission fiber bundle 248 when scope assembly 204 is rotated relative to camera assembly 202.

A second optical fiber taper 252 is shown in FIG. 4 for optically connecting transmission fiber bundle 248 to a light source 254. Taper 252 maximizes the light from light source 254 which can be transmitted through transmission fiber 248.

Now referring to FIG. 5, the details of the distal end of arthroscope 200 can be seen to include a probe, generally designated 256. Probe 256 includes cannula 228. Additionally, probe 256 includes a steel needle 258, a plurality of optical illumination fibers 260, and an optical fiber image guide 262. It is to be understood that needle 258 and illumination fibers 260 are substantially identical to the needle 56, fibers 34, and image guide 32, respectively, disclosed for arthroscope 10.

As shown, image guide 262 substantially defines a longitudinal axis 264, and the distal segment 266 of image guide 262 is bent at an angle 268 relative to image guide 262. Preferably, angle 268 is about twenty five (25) degrees. FIG. 5 also shows that a cylindrical GRIN rod 270 is attached to the distal end of image guide 266. Consequently, the axis 272 of GRIN rod 270 is oriented at an angle 268 to the axis 264 of image guide 262.

Referring briefly to FIG. 6, an iris 274 is shown at the distal base of GRIN rod 270. Preferably, iris 274 is an opaque material which is deposited onto GRIN rod 270. As shown in FIG. 6, iris 274 includes an aperture 276 through which light can pass. If desired, the side surface 278 of GRIN rod 270 can also be coated with an opaque material, to reduce the amount of stray light which can enter GRIN rod 270 through surface 278 and thereby interfere with image of the interior of the body surface under examination.

Referring back to FIG. 5, a clear epoxy material 280 is shown disposed within needle 258 in a surrounding relationship to image guide 262 and illumination fibers 260. Distal surface 282 of epoxy material 280 is preferably polished, and, as shown in FIG. 5, distal surface 282 is contoured to optimize light transmission out of illumination fibers 260 and onto image guide 262. More specifically, portion 284 of surface 282 is substantially parallel to distal base 286 of GRIN rod 270, to optimize light transmission into distal base 286. For increasing the illumination of the interior body structure under examination, portion 288 of surface 282 is oriented for maximizing the refractive angle of light which exits illumination fiber 260b. As shown, portion 288 of distal surface 282 of epoxy material 280 lies in a plane 290 that forms an angle 292 of about fifty degrees with the axis 264 of image guide 262.

FIG. 4 also shows that a flexible protective sheath 300 can be provided which maintains the sterility of the arthroscope 10 during its use. Specifically, a raised ring 302 is formed on the retainer ring 210 and a slip ring 304 is engaged with the raised ring 302. The sheath 300, which is attached to slip ring 304 is then draped over the camera assembly 202 and any other reusable components of the arthroscope 10 which are likely to be septic. Accordingly, the sterilized portions of arthroscope 10, which are also disposable can be joined with the reusable camera assembly 202 which is covered by the sheath 300.

Operation

In the operation of arthroscope 10, reference is initially made to FIGS. 1 and 2. Cannula assembly 68 with attached cannula 64 is detached from scope assembly 80. A trocar (not shown) is positioned through cannula 64, and the trocar is inserted into knee 14 to establish the entry site 14 for cannula 64. Once cannula 64 has been inserted into knee 14, the trocar can be removed from cannula 64. Disposable scope assembly 80 can then be attached to camera assembly 100, and camera assembly 100 placed in light communication with lamp 20. Also, camera assembly 100 is electrically connected to CCU 24. The disposable scope assembly and attached camera assembly 100 are inserted into cannula 64 to establish probe 30, and cannula assembly 68 is engaged with scope assembly 80.

When probe 30 has been inserted into knee 14 as disclosed and disposable scope assembly 80 has been attached to camera assembly 100, scope assembly 80 can be rotated clockwise and counterclockwise relative to camera assembly 100 to selectively focus the camera on the back of the image guide 32. More particularly, in reference to FIGS. 7 and 8, when scope assembly 80 is rotated relative to camera assembly 100, image guide 30 is rotated about its axis 44, as indicated by arrow 294. Recall that front tube 96 (and, hence, image guide 30) can be rotated ±170° relative to axis 44, so that the angle represented by arrow 294 in FIG. 8 is approximately 340°. Thus, image guide 30 can be rotated through 340°. As image guide 30 rotates, distal base 54 of GRIN rod 48 moves through a donut-shaped swath, and the viewing area 296 through which light can pass to enter distal base 54 moves through a relatively large region 298. Consequently, light from a relatively large region of knee 14 can enter distal base 54 of GRIN rod 48, and the image of this light processed by arthroscope 10 as described above for display on CRT 26 and recording by VCR 28. After the examination of patient 16, scope assembly 80 can be detached from camera assembly 100 and disposed of in a suitable receptacle, and a new scope assembly (not shown) engaged with camera assembly 100 for permitting the examination of another patient with arthroscope 10.

The operation of arthroscope 200 is in all essential respects identical to the operation of arthroscope 10, with the exception that cannula assembly 206 can rotate relative to scope assembly 204. Stated differently, scope assembly 204 can be rotated relative to cannula assembly 206, i.e., cannula assembly 206 can remain rotationally stationary with respect to the operator of arthroscope 200. By permitting cannula assembly 206 to remain stationary relative to the operator of arthroscope 200, fluid line 230 also remains stationary relative to the operator of arthroscope 200. Consequently, fluid line 230 will not become wrapped around cannula assembly 206 and will accordingly not unduly interfere with the operation of arthroscope 200.

While the particular arthroscope as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

We claim:

1. A hand-held diagnostic arthroscope for examining an internal structure of a body, which comprises:
   a camera assembly with a light focusing means;
   an image guide having a distal end and a proximal end, said image guide defining a first axis;
   a hollow tubular needle surrounding said image guide;
   an illuminating means joined with said image guide to establish a probe rotatably mounted on said camera assembly for insertion into the body;
   a lens attached to said distal end of said image guide for gathering light from said illuminating means, said lens defining an optical axis oriented at an oblique angle relative to said first axis;

a camera head positioned in said camera assembly in light communication with said proximal end of said image guide for generating a visual display signal of the internal structure of the body illuminated by said illuminating means; and a scope assembly attached to an end of said camera assembly for supporting said probe and connecting said probe to said camera assembly said image guide extending through said scope assembly and juxtaposed with said focusing means.

2. A hand-held diagnostic arthroscope for examining an internal structure of a body as recited in claim 1, wherein said probe further comprises a hollow tubular cannula having a lumen, said needle being positioned in said lumen coaxially with said cannula to establish an annular fluid passageway between said needle and said cannula, and said arthroscope further comprises a source of liquid attached in fluid communication with said passageway for bathing said internal structure of said body with said liquid.

3. A hand-held diagnostic arthroscope for examining an internal structure of a body as recited in claim 1, further comprising a video device electrically connected to said camera head for generating a video display representative of said video signal.

4. A hand-held diagnostic arthroscope for examining an internal structure of a body as recited in claim 3, wherein said lens is a gradient refractive index (GRIN) rod, said image guide is an optical fiber, and said guiding means includes a plurality of optical illuminating fibers in light communication with a quartz halogen lamp.

5. A hand held diagnostic arthroscope for examining an internal structure of a body as recited in claim 4, further comprising a cannula assembly surroundingly attached to said cannula and rotatably engaged with said scope assembly.

6. A hand-held diagnostic arthroscope for examining an internal structure of a body as recited in claim 1, wherein said light focussing means is axially movable within said camera assembly for focussing light from said image guide.

7. A hand-held portable arthroscope, which comprises:

an elongated probe having a proximal end and a distal end insertable into a body for examining the internal structure thereof, said probe comprising means for guiding light for illuminating the internal structure, said probe further comprising image guiding means for gathering light from the internal structure and guiding the light through said probe, said image guiding means having a proximal segment and a distal segment oriented at an oblique angle to said proximal segment;

a hand-held camera assembly for supporting said probe, said camera assembly being rotatable relative to said probe, said camera assembly including a camera head in light communication with said image guiding means for generating a signal representative of the light from the internal structure, said camera assembly having a distal end; and a light focussing means positioned in said camera assembly and a disposable scope assembly rotatably attached to said distal end of said camera assembly for connecting said probe to said camera assembly and for rotating said image guiding means relative to said camera head, said image guiding means extending through said scope assembly and juxtaposed with said focussing means when said scope assembly is attached to said distal end of said camera assembly.

8. A hand-held portable arthroscope as recited in claim 7, wherein said image guiding means is an optical fiber image guide substantially defining a first axis and said distal segment of said image guide includes a cylindrical gradient refractive index (GRIN) rod substantially defining a second axis, said second axis forming an acute angle relative to said first axis, and said means for guiding light for illuminating the internal structure is a plurality of optical fibers positioned next to said image guide.

9. A hand-held portable arthroscope as recited in claim 7, wherein said probe further comprises a tubular needle surrounding said image guide for supporting said image guide and a hollow tubular cannula having a lumen, said needle being positioned in said lumen coaxially with said cannula to establish an annular fluid passageway between said needle and said cannula, and said arthroscope further comprises a source of liquid attached in fluid communication with said passageway for bathing said internal structure of said body with said liquid.

10. A hand-held portable arthroscope as recited in claim 7, wherein said light source is a quartz halogen lamp, and said light focussing means is axially movable within said camera assembly for focussing light from said image guide.

11. A method for examining the internal structure of a body, which comprises the steps of:

electrically attaching a video display to a device which comprises:

a camera assembly with a light focusing means; an image guide having a distal end and a proximal end, said image guide defining a first axis; an illuminating means joined with said image guide including a hollow tubular needle surrounding said image guide to establish a probe rotatably mounted on said camera assembly for insertion into the body; a lens attached to said distal end of said image guide for gathering light from said illuminating means, said lens defining an optical axis oriented at an oblique angle relative to said first axis; a camera head positioned in said camera assembly in light communication with said proximal end of said image guide for generating a visual display signal of the internal structure of the body illuminated by said illuminating means and a scope assembly removably attached to a distal end of said camera assembly for supporting said probe and connecting said probe to said camera assembly said image guide extending through said scope assembly and juxtaposed with said focusing means; and inserting said probe into said body to examine the internal structure thereof.

* * * * *